US009322757B2

(12) United States Patent
Chen

(10) Patent No.: US 9,322,757 B2
(45) Date of Patent: Apr. 26, 2016

(54) MECHANICAL BEND, TWIST, PUSH AND PULL BLOWN OPTICAL CABLE TESTING APPARATUS

(71) Applicant: Verizon Patent and Licensing Inc., Arlington, VA (US)

(72) Inventor: David Z. Chen, Richardson, TX (US)

(73) Assignee: Verizon Patent and Licensing Inc., Basking Ridge, NJ (US)

( * ) Notice: Subject to any disclaimer, the term of this patent is extended or adjusted under 35 U.S.C. 154(b) by 235 days.

(21) Appl. No.: 14/209,398

(22) Filed: Mar. 13, 2014

(65) Prior Publication Data

US 2015/0260606 A1    Sep. 17, 2015

(51) Int. Cl.
*G01N 3/20* (2006.01)
*G01M 11/00* (2006.01)
*G01N 3/02* (2006.01)
*G01N 3/26* (2006.01)

(52) U.S. Cl.
CPC .............. *G01N 3/20* (2013.01); *G01M 11/30* (2013.01); *G01N 3/02* (2013.01); *G01N 2203/028* (2013.01)

(58) Field of Classification Search
CPC ...... G01M 11/30; G01M 11/088; G01N 3/20; G01N 3/26; G01N 2203/028; G01N 2203/0023; G01N 3/567
See application file for complete search history.

(56) References Cited

U.S. PATENT DOCUMENTS

| | | | | |
|---|---|---|---|---|
| 2,452,588 A * | 11/1948 | McFarland | ............... | G01N 3/34 73/158 |
| 2,657,573 A * | 11/1953 | Castricum | ............... | G01N 3/34 73/37 |
| 4,403,499 A * | 9/1983 | Sack | ........................ | G01N 3/32 73/158 |
| 6,550,323 B1 * | 4/2003 | Nguyen | .................... | G01N 3/34 73/158 |
| 6,591,692 B2 * | 7/2003 | Kawakita | ................. | G01N 3/20 73/810 |
| 7,926,358 B2 * | 4/2011 | Spehr | ........................ | G01N 3/32 73/849 |
| 8,443,680 B2 * | 5/2013 | Taylor, Jr. | ................ | G01N 3/22 73/849 |
| 8,783,115 B2 * | 7/2014 | Chen | ........................ | G01N 3/08 73/818 |
| 9,086,340 B2 * | 7/2015 | Yamamoto | .......... | G02B 23/2476 |
| 2002/0059834 A1 * | 5/2002 | Onoue | ...................... | G01N 3/32 73/812 |
| 2008/0134763 A1 * | 6/2008 | Moreno | .................... | G01N 3/32 73/49.5 |
| 2013/0293874 A1 * | 11/2013 | Goldstein | ........... | G01M 11/088 356/73.1 |
| 2014/0150566 A1 * | 6/2014 | Negro | ..................... | G01N 3/04 73/849 |

* cited by examiner

*Primary Examiner* — Lisa Caputo
*Assistant Examiner* — Punam Roy

(57) ABSTRACT

An apparatus, method, and system are disclosed for testing various properties of a sample, such as a cable or duct. The apparatus includes a duct and a plurality of radius controlling units. The radius controlling units are used to generate bends having a desired bending radius at different sections of the duct. Sensors are provided to measuring different forces and conditions of the sample or the duct. A controller can be provided for receiving sensor measurements and controlling various aspects of the test.

19 Claims, 4 Drawing Sheets

MECHANICAL BEND, TWIST, PUSH AND PULL BLOWN OPTICAL CABLE TESTING APPARATUS

BACKGROUND INFORMATION

Technological advancements often results in increased demands for the latest features, services, and content from consumers. This increased demand requires continuous upgrades in infrastructures in order to keep up the increased loads in, for example, data transmission. Such infrastructure upgrades often involve migration of voice and data communication services from metal (e.g., copper, aluminum, coaxial, etc.) to optical fiber (also referred to as fiber optics or simply fiber), as well as improvements in existing optical fiber lines. The increased use of optical fiber cables has also increased the need for reliability in the mechanical properties of such cables. For example, deployment of optical fiber cables in locations such as office buildings, apartment buildings, and single/multi-family homes often requires passage of the optical fiber cables within existing structures that can include complicated routes having numerous turns. Optical fiber cables, however, are more delicate than legacy cables, thereby making them more time consuming to deploy if the particular optical fiber cable is not properly selected. For example, the number of turns and bends present in the route can result in increased deployment time if the selected optical fiber cable does not meet the optimal requirements (e.g., size and bending properties) for a particular deployment route, thus resulting in additional costs. In addition, environmental conditions can cause damage to the optical fiber cable. When optical fiber cables are deployed, however, it is difficult to determine its mechanical properties or resistance to environmental conditions.

BRIEF DESCRIPTION OF THE DRAWINGS

Various exemplary embodiments are illustrated by way of example, and not by way of limitation, in the figures of the accompanying drawings in which like reference numerals refer to similar elements and in which.

DETAILED DESCRIPTION OF PREFERRED EMBODIMENTS

An apparatus, method, and system for testing various properties of a sample are described. In the following description, for the purposes of explanation, numerous specific details are set forth in order to provide a thorough understanding of the present invention. As is well known, the present invention may be practiced without these specific details or with an equivalent arrangement. In other instances, well-known structures and devices are shown in block diagram form in order to avoid unnecessarily obscuring the present invention.

Figure 1:
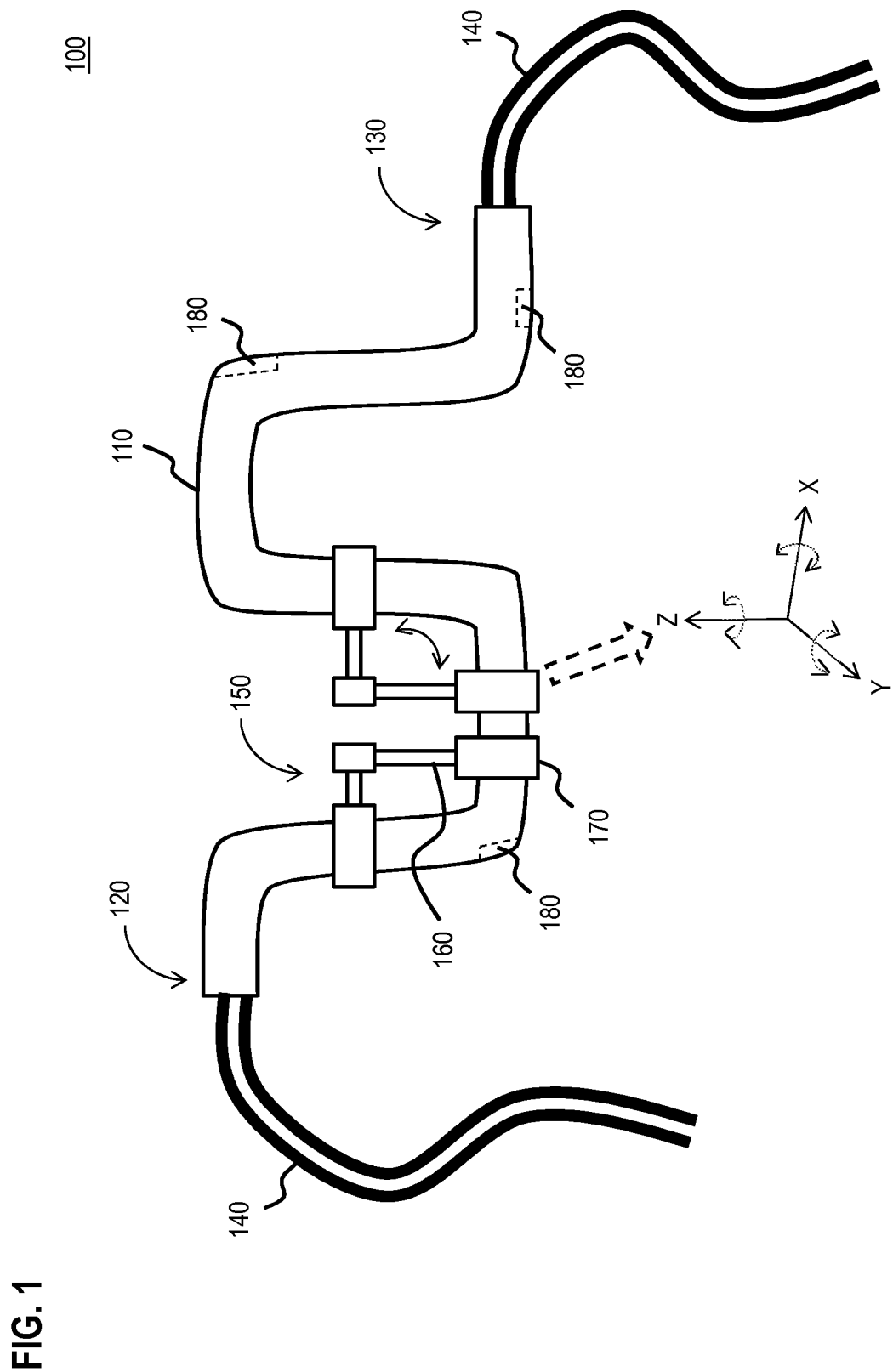
FIG. 1 is a diagram of a testing device, according to one embodiment.

FIG. 1 illustrates a testing device 100 for testing various mechanical properties of samples, such as, for example, an optical fiber cable, in accordance with at least one embodiment. The testing device 100 includes a duct 110 having a generally hollow interior. The duct 110 also includes a first end 120 and a second end 130. The duct 110 can be configured to have desired dimensions based on the sample 140 (or test sample) being tested and the specific tests being performed. For example, if the sample 140 being tested is an optical fiber cable, then the duct 110 can have a diameter which corresponds to a microduct for deploying the specific optical fiber cable. If the sample 140 being tested is an actual microduct, then the duct 110 can be appropriately sized to accommodate the microduct. Furthermore, if the test being performed require a large number of bends to simulate a deployment route, then the length of the duct 110 can be increased in order to accommodate all the bends.

As illustrated in FIG. 1, various radius controlling units 150 can be provided for forming bends at different sections of the duct 110. Each radius controlling unit 150 can include two arms 160 that are joined at one end. A brace 170 is connected to the free end of each arm 160 for receiving the duct 110 therein. The size of each brace 170 depends on the size of the duct 110 used to perform the tests. For example, a duct 110 configured for testing an optical fiber cable would require a smaller brace 170 than a duct 110 configured to test a microduct. According to an embodiment, the brace 170 can be adjustable in order accommodate different duct sizes.

According to at least one embodiment, the arms 160 can be pivotally connected in order to facilitate adjustment of the duct 110 at different angular configurations. Such angular configurations result in different bending radii on the duct 110. Furthermore, the bending radius of the duct 110 can be varied based on placement and orientation of one or more radius controlling units 150. Although FIG. 1 illustrates the radius controlling unit 150 as incorporating two arms, it should be noted that various embodiments provide for radius controlling units that are configured with a single arm capable of cooperating with other radius controlling units, based on position, to achieve a desired bending radius within the duct 110. Thus, over the length of the duct 110, multiple bends of varying bending radii can be formed in the duct 110 in order to perform the appropriate tests on the cables.

According to an embodiment, the radius controlling unit 150 can be configured to form both natural and unnatural bends in the duct 110. For example, a natural can correspond to a condition where no force, or a very small force, is applied to the duct 110 and it is allowed to bend naturally. A natural bend can also correspond, for example, to a condition where a force is applied at the first and second ends 120, 130 of the duct 110, and the remainder of the duct 110 is allowed to bend naturally. In contrast, an unnatural bend can correspond, for example, to actual deployment conditions which require large changes in direction within a short distance. For example, when routing the duct 110 through urban areas and/or buildings, it may be necessary to incorporate a bend of 90° or greater within a 1 foot displacement. In order to accommodate a variety of types of bends, the radius control units 150 can be configured for 3-dimensional rotation. Thus, as further indicated in FIG. 1, the arms 160 of the radius control units 150 can be configured to rotate about the XYZ axes of a 3-dimensional space.

FIG. 1 also illustrates a sample 140 (i.e., test sample) such as an optical fiber cable 140 disposed within the duct 110. The optical fiber cable extends from the first end of the duct 110 to the second end 130 of the duct 110. Depending on the specific test being performed, optical fiber cable may be cut to a length slightly longer than the duct 110, or only a required length may be dispensed removed from a spool (not shown) and inserted into the duct 110. According to an embodiment, a plurality of sensors 180 can also be provided within the duct 110 in order to measure various forces and mechanical conditions on the optical fiber cable, or other test sample. For example, the sensors 180 can be used to measure forces associated with bending, twisting, pushing, and pulling of the optical fiber cable. Additionally, the sensors 180 can be used to measure environment conditions existing within the duct 110. Once the tests have been concluded, the cable can be inspected for compliance with standard specifications.

Figure 2:
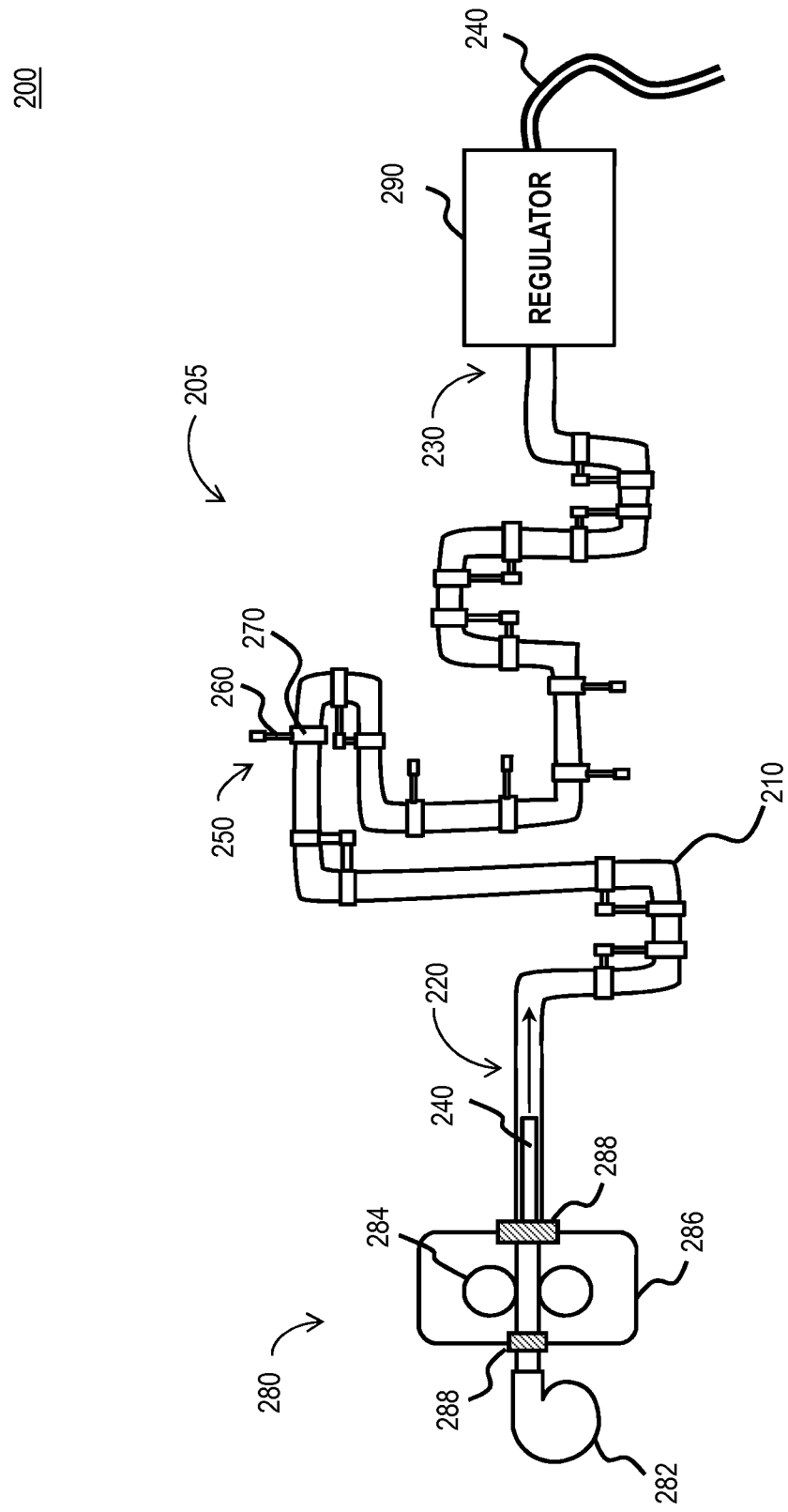
FIG. 2 is a diagram of a system for performing tests on a sample, according to one embodiment.

FIG. 2 illustrates a system 200 for performing tests on a sample 240, in accordance with at least one embodiment. As previously discussed, the sample 240 being tested can be in the form of a single cable, a cable having a jacket configured to carry a plurality of conductors and/or cables, optical fiber cables, etc. The system of FIG. 2 includes a testing device 205 consisting of a duct 210 having a generally hollow interior and a plurality of radius controlling units 250. The duct 210 includes a first end 220 wherein a sample 240, such as an optical fiber cable, enters and a second end 230 where the optical fiber cable exits. The plurality of radius controlling units 250 are used for generating the bends and turns required to perform the necessary tests on the cable.

As illustrated in FIG. 2, the radius controlling units 250 can be provided in different configurations depending on the length of the duct 210 and the complexity of the deployment route being recreated in by the duct 210. According to an embodiment, the radius controlling units 250 can include two arms 260 that are joined at one end. The arms 260 can be joined in a pivotal manner or a fixed manner, depending on specific requirements. A brace 270 is connected to the free end of each arm 260 for receiving the duct 210 therein. As previously discussed, the size of each brace 270 depends on the size of the duct 210 used to perform the tests. Furthermore, the brace 270 can be configured such that it is adjustable in order accommodate different duct sizes.

According to another embodiment, the radius controlling units 250 can be configured with a single arm 260 having one end secured to an external structure and a brace 270 at the other end for attachment to the duct 210. According to at least one embodiment, the radius controlling units 250 can be provided in a free floating manner. More particularly, the radius controlling units 250 can be configured such that they are only the two arms 260 are attached to the duct 210. Additionally, the opposite end of the arms 260 can be joined together permanently or adjustably in order maintain the desired bending radius. As will be discussed in greater detail below, the radius controlling units 250 can also be mounted in fixed locations for stability.

FIG. 2 also illustrates a jetting system 280 that can be connected to the first end 220 of the duct 210, according to an embodiment. The jetting system 280 supplies a flow of air at a predetermined pressure, as well as a pushing force, in order to blow the sample 240 through the first end 220 of the duct 210 toward the second end 230 of the duct 210. The jetting apparatus can be sized and configured to dispense various types of samples, including a cable, microduct, etc. According to at least one embodiment, the jetting apparatus can further include a dispenser 282 which houses a spool of the necessary sample 240 and one or more rollers 284 to feed the sample 240 through the duct 210. The rollers 284 are contained within in a housing 286 which is pressurized to generate an air jet into the duct 210. One or more seals 288 can be provided to maintain a required pressure as air is blown into the microduct 210.

The system of FIG. 2 also includes a regulator 290 that is provided at the second end 230 of the duct 210. The regulator 290 is configured to perform various actions that can affect deployment of the sample 240 within the duct 210. For example, according to at least one embodiment, the regulator 290 can vary the air pressure at the second end 230 of the duct 210 by controlling the amount of airflow allowed to exit. According to other embodiments, the regulator 290 can be configured to increase the level of resistance applied to the sample 240 exiting the second end 230 of the duct 210. This can be done in various ways. For example, the regulator 290 can be configured to increase the amount of friction between the sample 240 and the duct 210, thereby increasing the resistance level. Alternatively, the regulator 290 can be configured to provide a predetermined level of friction to the cable in order to generate the desired level of resistance.

According to at least one embodiment, the regulator 290 can vary the air pressure at the second end 230 of the duct 210 and/or vary the amount of resistance applied to the cable exiting the second end 230 of the duct 210 in order to simulate extended distances (or length of deployment) traveled by the test sample 240. More particularly, the system can be configured such that the length of the duct 210 corresponds to a fraction of an actual length that the cable will be deployed. For example, the duct 210 can have a length of 30 feet while the regulator 290 is operated to simulate forces that would result from deploying the cable over a length of, for example, 5 miles. Accordingly, deployment of the cable over a full range of realistic distances can be simulated using only a small section of the duct 210, according to an embodiment.

According to an embodiment, the system 200 of FIG. 2 can be used to optimize the selection of ducts 210, optical fiber cables 240, or both. More particularly, by selecting a duct 210 which corresponds to actual deployment duct, optical fiber cables 240 having different properties can be tested for optimal performance within the deployment duct. Alternatively, if a particular optical fiber cable 240 is necessary for the deployment route, different ducts 210 can be tested in order to optimize deployment. Furthermore, different combinations of ducts 210 and optical fiber cables 240 can be tested in order determine optimal combinations. Additionally, the optimization can factor the amount of time required to fully deploy a particular cable/duct combination.

Figure 3:
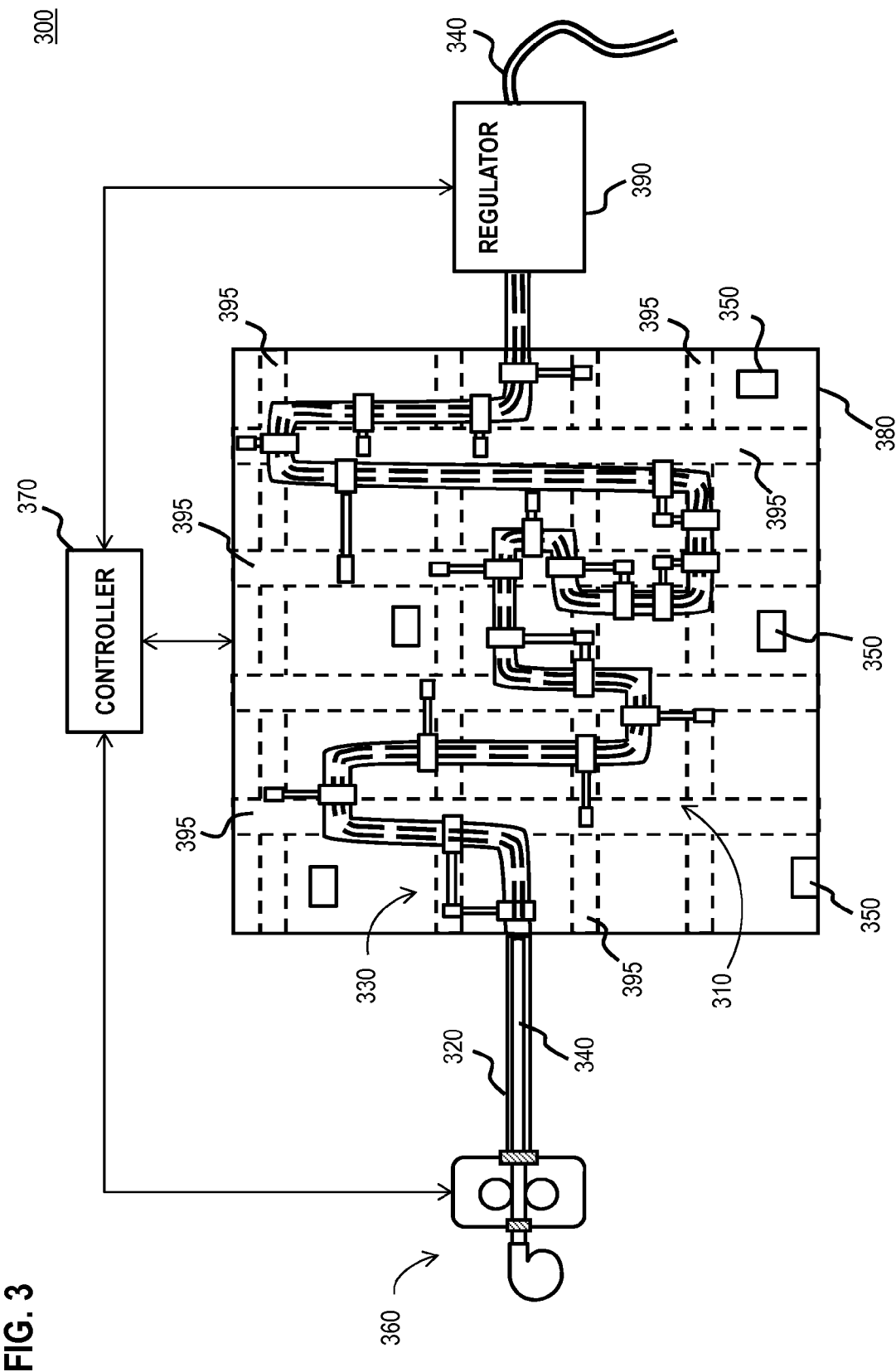
FIG. 3 is a diagram of a system for performing tests on a sample, according to another embodiment.

FIG. 3 illustrates a system 300 for testing samples 340 in accordance with one embodiment. The system 300 includes a testing device 310, a jetting system 360, a chamber 380, a regulator 390, and a plurality of sensors 350. A controller 370 can also be provided for controlling, at least in part, various operations of different components within the system 300. The testing device 310 includes a duct 320 having a generally hollow interior and a plurality of radius controlling units 330. The duct 320 includes a first end wherein the sample 340, such as an optical fiber cable, enters and travels toward the regulator 390. The plurality of radius controlling units 330 are used for generating the bends and turns required to perform the necessary tests on the cable, and can include one or more arms.

As illustrated in FIG. 3, a stabilizer assembly consisting of a plurality of mounting brackets 395 is provided for mounting the radius controlling units 330 thereon. The mounting brackets 395 provide a plurality of mounting points that can be used for securing the position of the radius controlling units 330. As such, the mounting brackets 395 are illustrated as having a general grid-like configuration, thereby allowing the radius controlling units 330 to the secured in a broad range of positions. Each mounting bracket 395 can be further provided on a rail which allows vertical and horizontal adjustments, thereby accommodating an increased number of locations for the radius controlling units 330. According to other embodiments, the stabilizer assembly can be configured such that the mounting brackets 395 are arranged in the form of a 3-dimensional unit in order to facilitate complex routing arrangements for the sample 340. Thus, according to various embodiments, extended deployment routes can be simulated within the chamber 380 by forming different bends and turns on the duct 320 to fully utilize (or saturate) the internal volume of the chamber 380.

The jetting apparatus is configured to supply an air jet at a predetermined pressure in order to blow the sample 340 through the duct 320. The jetting apparatus can include, for example, a dispenser for housing a spool of the necessary sample 340, and one or more rollers for feeding the sample 340 through the duct 320. The rollers are contained in a housing which is pressurized to generate an air jet into the duct 320. One or more seals can be provided to maintain a required pressure as air is blown into the duct 320.

According to the embodiment illustrated in FIG. 3, a chamber 380, such as an environmental chamber, is provided to enclose at least a portion of the duct 320. The chamber 380 can be configured as a 3-dimensional chamber, thereby providing an ability to create routes having turns in 3 dimensions. Additionally, the chamber 380 provides a seal which isolates the duct 320 from an outside environment. According to at least one embodiment, the chamber 380 can be used to simulate environmental conditions which the sample 340 is expected to endure during normal operations. As such, the chamber 380 can be equipped with various components capable of simulating different environmental conditions. For example, the chamber 380 can include a heater (not shown), a humidifier (not shown), an ultraviolet light generator (not shown), a water spray (not shown), etc. Accordingly, in addition to simulating deployment distances and obstacles, the system 300 can further simulate environmental conditions that can adversely affect performance of the sample 340.

According to the illustrated embodiment, various sensors 350 can be provided within the chamber 380. Such sensors 350 can be used to collect data pertaining to the environmental conditions being simulated within the chamber 380. As previously discussed, sensors 350 can also be provided within the duct 320 and/or the sample 340 in order to measure the effects of the environmental changes within on the sample 340 and duct 320. For example, according to an embodiment, sensors 350 can be provided within the sample 340 in order to measure the level of humidity under various conditions. Furthermore, the sensors 350 can be configured to measure condensation within the cable resulting from temperature changes within the chamber 380.

According to one or more embodiments, the controller 370 receives data collected by the sensors 350 and controls, at least in part, various operations of the jetting system 360, regulator 390, environmental generators, etc. For example, if a desired humidity of 80% is desired within the chamber 380, the controller 370 can monitor the sensor data in order to ensure that the humidity is adjusted to, and maintained at, the appropriate level. If the humidity level is below the required threshold, the controller 370 can operate the humidifiers within the chamber 380 in order to increase the level of humidity. Similarly, if the temperature of 120° F. is desired, the controller 370 can control operation of the heater (or plurality of heaters) to increase the temperature within the chamber 380 until the desired temperature is reached. At that point, the controller 370 would monitor the sensor data and vary the amount of heat generated in order to maintain the temperature at the desired level. According to other embodiments of the invention, however manual controls can also be provided for adjusting and maintaining environmental conditions within the chamber 380. Additionally, data collected by the sensors 350 can be supplied to various display units to allow an operator to visually determine conditions within the chamber 380 and make appropriate adjustments in order to achieve a desired set of conditions.

Figure 4:
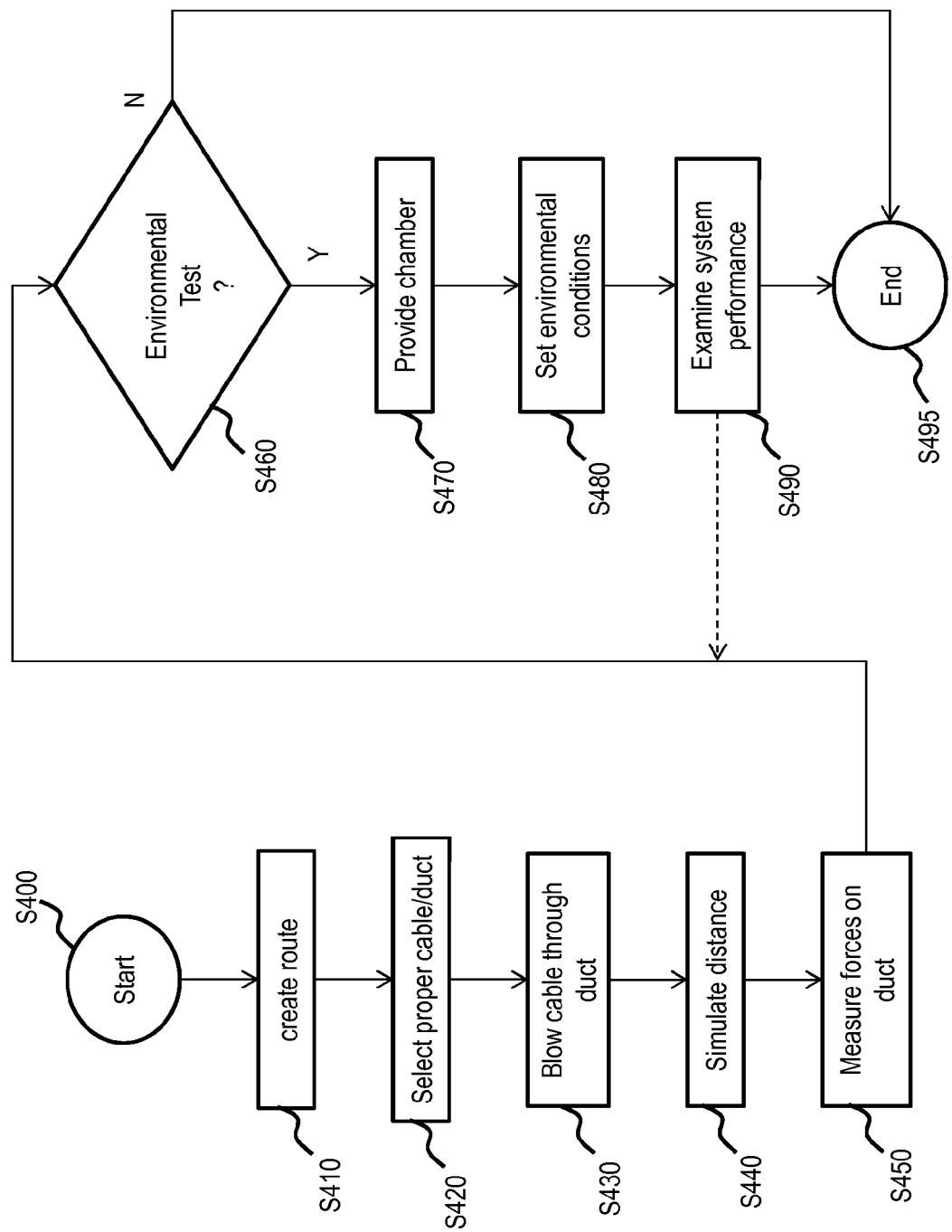
FIG. 4 is a flowchart of a process for performing tests on a sample, according to one embodiment.

FIG. 4 is a flowchart illustrating a method of testing a sample, such as a cable, in accordance with at least one embodiment. The process begins at S400, where the system is initialized and/or prepared for testing the sample. At S410, a route is formed using the duct. This can be accomplished, for example, by utilizing one or more radius controlling units to form at least one bend within the duct. As previously discussed, the route can be formed such that it simulates an actual deployment route which must be tested and/or optimized. The radius controlling units can therefore be used to apply multiple bends having various bending radii to the duct. Furthermore, extended deployment routes may be simulated within the chamber by incorporating bends in a 3-dimensional space so as to maximize the use of space within the chamber.

At S420, the proper cable selected for insertion within the duct. As previously discussed, optimal combinations of cable and duct can be determined for the desired deployment. According to an embodiment, proper cable selection entails consideration of the duct to be used in the deployment process as well as the cable size. For example, if the duct has a 10 mm diameter, then a cable having a diameter of 8 mm may be selected. It should be noted, however, that optimization of the cable/duct combination may result in a particular cable having a diameter of 9 mm. Accordingly, S420 is not limited to the diameter of the cable, but rather entails selection of a cable capable of operating at a desired performance level with a selected duct. Conversely, S420 can also entail selection of an appropriate duct, if a particular cable is necessary, thus setting a constraint. Furthermore, S420 and S410 may be may be sequence independent and/or performed jointly if the duct must also be selected with or without the cable in order to create the route.

At S430, the cable is blown through the duct using, for example, a jetting system. At S440, the deployment distance is simulated. According to at least one embodiment, the controller can be configured to control operation of the regulator in order to vary the air pressure at the second end of the duct in order to create forces corresponding to those experienced by the cable along the simulated distance. According to other embodiments, the controller can control operation of the regulator in order to increase the friction force on the cable in order to achieve the same level of resistance. According to still other embodiments, the controller can increase friction as well is vary the air pressure in order to achieve the desired results.

At S450, various forces that can affect the cable are measured. Furthermore, the length of time required to blow the cable through the entire length of the deployment route, or a portions thereof, can be determined. At S460, it is determined whether an environmental test is required. If no environmental test is required, then control is passed to S495, where the process ends. Alternatively, if environmental tests are required control passes to S470 where the chamber is provided to enclose the duct in order to create an isolated section for performing the environmental simulations. At S480, the environmental conditions are set. According to various embodiments, the environmental conditions being simulated can include heat, humidity, ultraviolet light exposure, etc. Furthermore, a length of time for exposing the cable to such conditions can be selected. Once the environmental conditions have been set, the controller operates various environmental generators (e.g., heater, humidifier, UV light generator, etc.) within the chamber in order to achieve the desired environmental test conditions. Furthermore, the controller maintains the test conditions over the desired testing interval. At S490, the cable is removed from the chamber and the duct, and the system performance is analyzed in order to assess whether the requirements for actual deployment have been bet. For example, the particular cable/duct combination may result in a deployment time which exceeds requirements of a particular locality. Additionally, the environmental tests may reveal excess moisture buildup within the duct, UV degradation, etc. Such conditions may require the test to be repeated using, for example, a different cable/duct combination. Depending on the results of the system performance, it may only be necessary to repeat the environmental test. Thus, optionally, the process can return to S460, or S410. The process then ends at S495.

In the preceding specification, various preferred embodiments have been described with reference to the accompanying drawings. It will, however, be evident that various modifications and changes may be made thereto, and additional embodiments may be implemented, without departing from the broader scope of the invention as set forth in the claims that follow. The specification and drawings are accordingly to be regarded in an illustrative rather than restrictive sense.

What is claimed is:

1. An apparatus comprising:
   a duct having a first end and a second end;
   one or more radius controlling units for forming one or more bends at one or more sections of the duct, each of the one or more bends having a desired bending radius;
   at least one force sensor for measuring forces exerted on a test sample; and
   a controller for receiving sensor measurements and controlling various conditions of the apparatus to conduct at least one test on the test sample; and
   a jetting apparatus for supplying an air jet at a predetermined pressure, and blowing the test sample through the first end of the duct and out of the second end of the duct.

2. An apparatus of claim 1, wherein the test sample is a microduct configured for receiving a cable therein.

3. An apparatus of claim 1, further comprising a stabilizer assembly for maintaining the duct in a fixed position while the at least one test is conducted on the test sample.

4. An apparatus of claim 1, further comprising at least one environmental sensor for measuring environmental conditions within the duct, the test sample, or both.

5. An apparatus of claim 1, further comprising:
   a regulator positioned at the second end of the duct for varying air pressure at the second end of the duct, varying friction between the test sample and the duct, or both,
   wherein the controller is configured to control operation of the regulator.

6. An apparatus of claim 5, wherein the controller is configured to control, at least in part, the jetting apparatus and the regulator to simulate extended distances traveled by the test sample.

7. A method comprising:
   forming at least one bend having a desired bending radius on a duct using one or more radius controlling units;
   applying an air jet through a first end of the duct using a jetting apparatus;
   blowing a test sample through the first end of the duct and toward a second end of the duct;
   measuring forces exerted on the test sample; and
   conducting at least one test on the test sample by controlling, using a controller, the air jet applied by the jetting apparatus based, to at least in part, on the measured forces.

8. A method of claim 7, further comprising maintaining the duct in a fixed position, using a stabilizer assembly, while the at least one test is performed on the test sample.

9. A method of claim 7, further comprising:
   varying, using a regulator, air pressure at the second end of the duct, friction between the test sample and the duct, or a combination thereof,
   wherein the regulator is controlled by the controller.

10. A method of claim 9, further comprising controlling the jetting apparatus and the regulator to simulate extended distances traveled by the test sample.

11. A method of claim 9, further comprising:
    enclosing at least a portion of the duct within a sealed chamber; and
    simulating predetermined environmental conditions within the chamber.

12. A method of claim 11, further comprising:
    measuring environmental conditions within the chamber, the duct, the test sample, or a combination thereof; and
    supplying the measured environmental conditions to the controller.

13. A system comprising:
    a testing apparatus including a duct having a first end and a second end, and one or more radius controlling units for forming one or more bends at one or more sections of the duct, each of the one or more bends having a desired bending radius;
    a jetting apparatus for supplying an air jet at a predetermined pressure, and blowing a test sample through the first end of the duct and toward the second end of the duct;
    a chamber enclosing at least a portion of the duct;
    a regulator positioned at the second end of the duct for varying air pressure at the second end of the duct, varying friction between the test sample and the duct, or a combination thereof;
    a plurality of sensors for collecting data within the system; and
    a controller for receiving the collected sensor data and conducting at least one test on the test sample by controlling, at least in part, operation of the jetting apparatus, the regulator, the chamber, or a combination thereof.

14. A system of claim 13, wherein the test sample is a microduct.

15. A system of claim 14, wherein a cable is disposed within the microduct.

16. A system of claim 13, further comprising a stabilizer assembly for maintaining the testing apparatus in a fixed position while the at least one test is conducted on the test sample.

17. A system of claim 13, wherein the controller is configured to simulate extended distances traveled by the test sample by controlling, at least in part, operation of the jetting apparatus and the regulator.

18. A system of claim 13, wherein the controller is configured to simulate different environmental conditions by controlling, at least in part, operation of the environmental chamber.

19. A system of claim 13, wherein the collected sensor data includes forces exerted on the test sample, environmental conditions within the chamber, environmental conditions within the duct, environmental conditions within the test sample, or a combination thereof.

* * * * *